US00RE37207E

(19) United States
(12) Reissued Patent
Cronce

(10) Patent Number: US RE37,207 E
(45) Date of Reissued Patent: Jun. 5, 2001

(54) DECONTAMINATION SOLUTION AND METHOD

(75) Inventor: Donald T. Cronce, Fredericksburg, VA (US)

(73) Assignee: The United States of America as represented by the Secretary of the Navy, Washington, DC (US)

(21) Appl. No.: 09/573,152

(22) Filed: May 19, 2000

Related U.S. Patent Documents

Reissue of:
(64) Patent No.: 5,859,064
Issued: Jan. 12, 1999
Appl. No.: 08/989,271
Filed: Dec. 11, 1997

U.S. Applications:

(63) Continuation-in-part of application No. 08/615,348, filed on Mar. 13, 1996, now Pat. No. 5,760,089.

(51) Int. Cl.[7] ..... A61K 31/14; B01D 11/02
(52) U.S. Cl. ..... 514/643; 210/690; 210/755; 210/759
(58) Field of Search ..... 514/643; 210/690, 210/755, 759

(56) References Cited

U.S. PATENT DOCUMENTS

| | | | | |
|---|---|---|---|---|
| 2,010,183 | * | 4/1935 | McFarlane | 536/27 |
| 2,131,210 | | 9/1938 | Baird et al. | 564/75 |
| 2,555,504 | | 6/1951 | Noll | 514/643 |
| 2,555,604 | * | 8/1951 | Noll | 514/643 |
| 3,620,807 | | 11/1971 | Murray | 564/291 |
| 3,962,332 | | 6/1976 | Trapasso | 564/204 |
| 4,022,911 | | 5/1977 | Goldhaft et al. | 424/329 |
| 4,661,523 | | 4/1987 | Disch et al. | 514/635 |
| 4,672,069 | | 6/1987 | Sommer et al. | 514/348 |
| 4,672,089 | * | 6/1987 | Sommer et al. | 514/348 |
| 4,672,122 | | 6/1987 | Sommer et al. | 546/292 |
| 4,744,917 | | 5/1988 | Scardera et al. | 252/187.28 |
| 4,784,699 | | 11/1988 | Cowsar et al. | 134/42 |
| 4,798,870 | | 1/1989 | Lyle, Jr. et al. | 525/327.1 |
| 4,850,729 | | 7/1989 | Kramer et al. | 401/183 |
| 4,874,532 | | 10/1989 | Worley | 210/755 |
| 4,883,608 | | 11/1989 | Trujillo et al. | 252/189 |
| 4,914,132 | | 4/1990 | Donofrio et al. | 514/643 |
| 5,010,183 | | 4/1991 | Macfarlane | 536/27 |
| 5,019,173 | | 5/1991 | Getungs et al. | 134/4 |
| 5,075,287 | * | 12/1991 | Dannard et al. | 514/183 |
| 5,075,297 | | 12/1991 | Bannard et al. | 514/183 |
| 5,116,512 | | 5/1992 | Bartram et al. | 210/690 |
| 5,116,612 | * | 5/1992 | Bartram et al. | 210/690 |
| 5,504,113 | | 4/1996 | Lucero | 514/554 |

FOREIGN PATENT DOCUMENTS

| | | |
|---|---|---|
| 2041206 | 7/1992 | (RU) . |
| WO95/13122 | 5/1995 | (WO) . |

OTHER PUBLICATIONS

"Sulfonation and Sulfation to Thorium and Thorium Compounds", Kirk Othmor Encyclopedia of Chemical Technology, vol. 22, 3rd Edition, ed. John Wiley & Sons, Inc., pp. 383–385, 1983.

Yang, Y–C. et al, "Decontamination of Chemical Warfare Agents", Chem. Rev., 82 (8): 1729–1743, 1992.

* cited by examiner

*Primary Examiner*—Deborah C. Lambkin
(74) *Attorney, Agent, or Firm*—James B. Bechtel, Esq.; Wyatt B. Pratt, Esq.

(57) ABSTRACT

A chemical warfare agent decontamination solution made up of about 20% of a quaternary ammonium complex containing benzyltrimethylammoniumchloride and benzyltriethylammonium chloride and about 20% by weight of an oxidizer, dissolved in a solvent, such as water or glycol, is provided. This solution is a noncorrosive, nontoxic, nonflammable decontaminant, which may also be used to neutralize organophosphorus agricultural chemicals.

21 Claims, No Drawings

DECONTAMINATION SOLUTION AND METHOD

Matter enclosed in heavy brackets [ ] appears in the original patent but forms no part of this reissue specification; matter printed in italics indicates the additions made by reissue.

CROSS-REFERENCE TO RELATED APPLICATION

This is a continuation-in-part of U.S. patent application Ser. No. 08/615,348, filed Mar. 13, 1996, U.S. Pat. No. 5,760,089.

FIELD OF THE INVENTION

This invention relates generally to the field of compositions useful in decontamination of material, equipment and personnel exposed to chemical warfare agents.

BACKGROUND OF THE INVENTION

Methods for decontamination of chemical warfare agents, which include a variety of organophosphorus and organosulfur compounds, are known in the art. However, these known methods use compositions which have certain undesirable properties, including corrosiveness, flammability and toxicity. For example, hypochlorite formulations are very corrosive and toxic. Additionally, many decontaminants degrade upon exposure to water and carbon dioxide, requiring that these solutions be prepared and used the same day they are needed. Further, application of the hypochlorite decontaminant often requires substantial scrubbing for removal and destruction of the chemical warfare agent, a procedure which limits its use.

One decontaminant, Decontamination Solution 2 (DS2), is useful against a variety of agents and contains 70% diethylenetriamine, 28% ethylene glycol monomethyl other and 2% sodium hydroxide. However, DS2 will spontaneously ignite upon contact with hypochlorites and hypochlorite-based decontaminants. Further, DS2 may cause corrosion to aluminum cadmium, tin, and zinc after prolonged contact, and softens and removes paint.

A need exists for a chemical warfare agent decontamination solution which is, noncorrosive, nontoxic, nonflammable, and environmentally safe.

SUMMARY OF THE INVENTION

The invention provides a chemical warfare agent decontamination composition comprising about 15 to about 25%, by weight of a quaternary ammonium complex and about 15 to about 25%, by weight of an oxidizer, in a non-toxic, non-flammable solvent. The composition is desirably adjusted to a pH between about 8 and about 12. Depending on the solvent selected, the decontaminant of the invention may optionally contain corrosion inhibitors, stabilizers, buffers, catalysts and the like. Advantageously, this composition is nontoxic, noncorrosive and non-flammable.

In a preferred embodiment, the quaternary ammonium complex consists of a mixture of benzyltrimethylammonium chloride and benzyltriethylammonium chloride, the oxidizer is hydrogen peroxide, the solvent is water, and pH is between about 8 and 10. In an alternative embodiment, the solvent is a diol.

In another aspect, the invention provides a method for decontaminating chemical warfare agents comprising applying a chemical warfare agent decontaminant as described herein to a contaminated surface.

Other aspects and advantages of the present invention are described further in the following detailed description of the preferred embodiments thereof.

DETAILED DESCRIPTION OF THE INVENTION

The present invention provides a chemical warfare agent decontamination formulation containing a quaternary ammonium complex (QAC) and an oxidizer solvated in a non-corrosive, non-toxic and non-flammable solution; the decontaminant is preferably adjusted to a pH between about 8 and about 12. The decontaminant of the invention is non-flammable. Advantageously, the reaction of the decontaminant of the invention with chemical warfare agents, including VX, GD and HD, occurs very rapidly.

The decontaminant of the invention contains between about 15% to about 25%, by weight, of a QAC. As defined herein, a QAC has the general structure provided below.

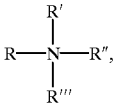

where R, R', R", and R'" are any alkyl or aryl organic species capable of chemically bonding to the nitrogen atom, N, through a carbon atom. Preferred QAC for use in preparing the decontaminant of the invention are the chloride salts of benzyltriethylammonium (R is benzyl and R', R", and R'" are —$CH_2CH_3$) and benzyltrimethylammonium (R is benzyl and R', R" and R'" are —$CH_3$). In a preferred embodiment, the decontaminant of the invention contains a mixture of benzyltrimethylammonium chloride and benzyltriethylammonium chloride in a ratio of about 5 parts to about 1 part, by weight, respectively. Desirably, the benzyltrimethylammonium chloride makes up between about 10% to about 20%, by weight of the decontaminant solution and the benzyltriethylammonium chloride makes up about 3% to about 10%, by weight of the decontaminant solution. Alternatively, one of skill in the art may readily substitute other appropriate salts for the chloride salt of the QAC. Particularly preferred salts include the hydroxide salts.

The selected QAC is mixed with a suitable non-inflammable, non-corrosive, nontoxic solvent. Preferably, this solvent is water, which is present in an amount between about 25% to about 35%, by weight, of the decontaminant and, more preferably, about 30% by weight of the decontaminant. In another embodiment, the solvent is a diol. One particularly desirable diol is 1,2-propanediol (propylene glycol). However, other diols capable of solvating both polar and low-polarity compounds may be readily substituted. For example, suitable diols may include other 1,2-alkanediols, particularly where the alkane is butane, pentane or hexane. Where the solvent used is propylene glycol, it is preferably present in an amount of about 15 to 25%, by weight, of the composition, i.e., roughly equivalent to the weight percentage of the QAC present in the composition.

Advantageously, the inventor has found that the use of an oxidizer in combination with the QAC of the invention provides a decontaminant which works quickly and effectively to solvate and neutralize chemical warfare agents, and works particularly well for neutralization of organosulfur agents such as mustard gas (HD), and organophosphorus agents such as the nerve agents termed VX and GD. Thus, the decontaminant of the invention contains an oxidizer. In a currently preferred embodiment, the oxidizer is hydrogen peroxide. Other suitable oxidizers include other peroxy or hydroperoxy compounds, including, e.g., the acids and salts of peracetate, perborate monohydrate, perborate tetrahydrate, monoperoxyphthalate, peroxoymonosulfate, peroxydisulfate, and percarbonate. Still other suitable oxidizers may be readily selected from among those which are compatible with the remainder of the components present in the decontaminant. Generally, the oxidizer is present in an amount between about 15 to about 25% (by weight), and more preferably, about 20%, by weight, of the total weight of the decontaminant.

Suitably, the decontaminant containing the QAC and oxidizer is provided with a pH of between about 8 and about 12, and more preferably, between about 8 and 10. Suitable acids for lowering the pH (increasing acidity) and bases for raising pH (increasing alkalinity) may be readily selected by one of skill in the art.

The decontaminant may also contain stabilizers which alone, or in combination with the pH adjuster, prevent reaction of the oxidizer with the other components of the formulation without inhibiting the ability of the decontaminant to solvate and neutralize chemical warfare agents. Where the stabilizer is used in conjunction with a separate pH adjuster, the stabilizer is preferably selected from among those which do not significantly alter the pH of the decontaminant. Suitable stabilizers may be readily selected by one of skill in the art, taking into consideration the selected oxidizer and the other components in the decontaminant formulation. For example, where the oxidizer is hydrogen peroxide, the stabilizer is preferably acetanilide. Generally, these stabilizers are present in an amount of less than about 1% of the decontaminant.

The decontaminant of the invention may contain a corrosion inhibitor. Suitable corrosion inhibitors include amino alcohols, such as 2-amino-2-methyl-1-propanol. One of skill in the art may substitute other non-toxic corrosion inhibitors, which may be selected from among primary amines and polyamines. For example, when the decontaminant of the invention is water-based, as described herein, a corrosion inhibitor is required and may also be used as a solvent. In such a formulation, the corrosion inhibitor may be found in an amount up to about 55%, by weight, of the decontaminant. Alternatively, when the solvent is a diol, the corrosion inhibitor may make up less than about 10%, by weight, of the decontaminant formulation.

In addition to the corrosion inhibitor, the decontaminant of the invention may optionally contain preservatives, buffers, and reaction catalysts. Such components, and the required amounts thereof, are well known and can be readily selected by one of skill in the art. See, e.g, Yang, et al., Chem. Rev., 92(8):1729 (1992).

A particularly preferred decontaminant formulation of the invention is provided below. The approximate weight percentages of the components of one preferred formulation is provided in the Table below. Isobutanolamine (also 2-amino-2-methyl-1-propanol) is a corrosion inhibitor. Column 2 identifies the number of the component by reference to its accession number in Chemical Abstracts Service.

TABLE 1

| Component | CAS Number | Weight Percent |
|---|---|---|
| Benzyltrimethyl ammonium chloride | 56-93-9 | 10–20 |
| Benzyltriethyl ammonium chloride | 56-37-1 | 3–10 |
| Oxidizer | | 15–20 |
| isobutanolamine | 124-68-5 | 25–35 |
| Water | | 25–35 |

The decontaminant compositions of the invention are nontoxic and useful in detoxifying/neutralizing a variety of chemical warfare agents, including organosulfur agents such as mustard gas (HD), and organophosphorus agents such as the nerve agents termed VX and GD. The decontaminants of the invention may also be used to neutralize selected organophosphorus agricultural chemicals. Decontamination is effected by applying a decontaminant of the invention to the contaminated material, equipment, personnel, or the like. Such application may be spraying, showering, washing or other suitable means.

The amount of decontaminant required under field conditions can be readily determined by one of skill in the art. The decontaminant is typically used in a ratio approaching or exceeding at least about 100:1 decontaminant:chemical agent. However, it has been tested under laboratory conditions at a much lower ratio of decontaminant to agent.

These examples illustrate the preferred methods for preparing and applying the decontaminant of the invention. These examples are illustrative only and do not limit the scope of the invention.

EXAMPLE 1

Decontamination Formulations

A. OAC/Oxidizer Decontaminant

A currently preferred decontaminant composition of the invention contains the following components:

| Component | Weight Percent |
|---|---|
| Benzyltrimethylammonium chloride | 16 |
| Benzyltriethylammonium chloride | 4 |
| Hydrogen Peroxide | 20 |
| Isobutanolamine | 30 |
| Water | 30 |
| Total: | 100 |

The decontaminant was prepared as follows. Because of their hygroscopic natures, benzylmethylammonium chloride (28.1 g) and benzyltriethylammonium chloride (6.1 g) were oven dried before use. These compounds were then added to a heated (about 45° C.) mixture of water (3 g) and isobutanolamine (56.1 g). The final mixture was stirred until the solid components have dissolved.

The composition is adjusted to a pH of 9±0.15 with concentrated hydrochloric acid, and mixed 4:1 w/w with 35% hydrogen peroxide. The final product was a clear golden color.

This formulation was used in the neutralization studies in Example 2 below. Two formulations which contained no oxidizer were prepared as described in sections B and C below for use in comparative studies. These formulations are described in detail in co-pending parent application U.S. patent application Ser. No. 08/615,348, filed Mar. 13, 1996, which is incorporated by reference herein.

B. Diol-Based Formulation

Benzyltrimethylammonium chloride (55 g) and benzyltriethylammonium chloride (15 g) were oven dried before use. Along with sodium perborate tetrahydrate (2 g), they were then added to a heated (about 45° C.) mixture of propylene glycol (68 g) and 2-amino-2-methyl-1-propanol (12 g). The propylene glycol-2-amino-2-methyl-1-propanol solution was heated to aid the dissolution of the sodium perborate tetrahydrate without it decomposing (sodium perborate tetrahydrate decomposes at about 60° C). The final mixture was stirred until the solid components have substantially dissolved. The mixtures were removed from the stirring and allowed to remain undisturbed. More solid dissolved while undissolved solids settled out of solution. When no more solid dissolved, the solution was decanted then stored in a sealed container. The decanted solution was clear with a golden color.

C. Water-Based Decontaminant Formulation

Benzyltrimethylammonium chloride (90 g) and benzyltriethylammonium chloride (25 g) were oven dried before use. They were added to a heated solution of 2-amino-2-methyl-1-propanol (185 g) and water (20 g). Sodium perborate tetrahydrate (2 g) was then added. This solution was treated similarly to the diol-based solution described in Example 1B. The pH of the decanted solution was adjusted to about 10.6 (about 20 g water was added).

EXAMPLE 2

Neutralization of VX

A QAC/oxidizer decontaminant of the invention was prepared as described in Example 1A above and used at a dilution of 20:1 w/w decontaminant:VX. For comparative purposes, a decontaminant containing a QAC mixture, but no oxidizer (prepared as described in Example 1C above was used at a dilution of 10:1 w/w decontaminant:VX.

The neutralization reactions were conducted under ambient conditions. 0.1 mL of VX (CAS Registry No. 50782-69-9) in a 13×100 mm culture tube was immediately Vortex mixed upon addition of 1.0 or 2.0 mL decontaminant. A 0.025 mL aliquot of the mixture was immediately withdrawn, and then added to and mixed with 4.97 mL 0.2M sodium dihydrogen phosphate to quench the reaction. Serial dilutions, using deionized water, were made to bring the concentration of the quenched reaction mixture into the analytical range of the acetylcholinesterase inhibition method (0.0002 micrograms). Additional 0.025 mL aliquots of the original mixture were withdrawn after specified time periods, and treated and analyzed in the manner just described. The acetylcholinesterase inhibition method determines the rate of change of the acetylcholinesterase enzyme activity; the rate of change of the enzyme activity, determined spectroscopically, is directly related to the amount of VX present in the 0.025 mL aliquot. Using this result with the amount of VX originally present in the aliquot, the percent neutralization was determined by an acetylcholinesterase inhibition method performed as follows. However, other assays may be used. Several diagnostic kits are commercially available (e.g., through Sigma Chemical Corporation of St. Louis, Mo.).

The method used in these analyses involved several stock solutions. A buffer concentrate consisting of 18.2 g tris-(hydroxymethyl) aminomethane and 31.4 g 3-(n-morpholino)-propane sulfonic acid MOPS in 100 mL water at pH=7.8 was prepared. An enzyme stock (refrigerated) was prepared by adding a small, unmeasured quantity of lyophilized enzyme in 10 mL water containing 0.3 mL of the buffer concentrate and 100 mg bovine serum albumin. An enzyme working solution (refrigerated) was prepared by diluting the enzyme stock solution (with the buffer/albumin solution) to produce a 0.5–0.6 change in absorbance in 1 minute at 412 nm. A substrate concentrate (refrigerated) contained 200 mg acetylthiocholine iodide in 10 mL water. Finally, a DTNB solution (refrigerated) was made by dissolving 40 mg 5,5'-dithiobis-(2-nitrobenzoic acid) in 0.6 mL buffer concentrate and diluted with water to 20 mL, and then adding 350 mg calcium chloride and 640 mg magnesium chloride hexahydrate.

To determine the activity inhibition of the test sample, 0.1 mL of buffer concentrate and 0.005 mL enzyme working solution was added to 2.0 mL water. The sample was then incubated for 6 minutes in a 30° C., water bath. Following addition of 1.0 mL of the test sample and mixing, the sample was incubated for an additional 10 minutes. Finally, 0.1 mL DTNB and 0.05 mL substrate solutions were added. Immediately following mixing, the absorbance change was measured at 412 nm for 1 minute.

The results are provided below.

| Elapsed Time | QAC/OXIDIZER Composition | Control |
|---|---|---|
| <30 seconds | 37% | 5% |
| 30 minutes | 95% | 20% |
| 1 hour | 99+% | 27% |

These results indicate that a decontaminant of the invention will provide good neutralization when used at a ratio achievable under field conditions.

EXAMPLE 3

Neutralization of Chemical Warfare Agents

The following assays were used to assay the ability of the decontaminants described herein to neutralize HD (sulfur mustard) and GD. The decontaminant:agent w/w ratios are 50:1 for HD and 20:1 for GD.

A. HD Neutralization Assay

The neutralization reactions were conducted under ambient conditions as follows. 150 mg of HD (sulfur mustard, CAS Registry No. 505-60-2) in a 13×100 mm culture tube was immediately Vortex mixed upon addition of 1.0 mL decontaminant. A 0.025 mL aliquot of the mixture was immediately withdrawn, and then added to and mixed with 1.0 mL n-butanol to quench the reaction. Serial dilutions, using n-butanol, were made to bring the concentration of the quenched reaction mixture into the analytical range of the DB-3 colorimetric analytical method (0.5–20 micrograms HD). Additional 0.025 mL aliquots of the original mixture were withdrawn after specified time periods, and treated and analyzed in the manner just described. The DB-3 method determines the amount of unneutralized HD; using the DB-3 result and the amount of HD originally present in the 0.025 mL aliquot, the percent neutralization was calculated.

The DB-3 method was performed as follows. The DB-3 concentrate was prepared by mixing equal volumes of a solution of 336 mg/mL sodium perchlorate in distilled water and a solution of 24 mg/mL 4-(p-nitrobenzyl pyridine) in methyl cellosolve. The pH of the concentrate was adjusted to 6.5–7.5 with concentrated MOPS and the concentrate was refrigerated.

1.0 mL of the final n-butanol solution described earlier was mixed with 1.0 mL diethyl phthalate and 1.0 mL DB-3 concentrate and shaken vigorously. The solution was heated 15 minutes in boiling water bath, then cooled in a room temperature water bath. Immediately following the addition of 0.5 mL diethylamine, the absorbance was measured at 575 nm. The intensity of the resulting purple color was directly proportional to the amount of HD present in solution.

Early results have shown that the decontaminant of the invention neutralized 20% of the agent within 30 seconds and 66% within one hour.

B. Neutralization of GD

These neutralization reactions were performed as described in Example 2 above substituting GD (soman, CAS Registry No. 96-64-0) for VX. Early results have shown that the decontaminant of the invention neutralized 99+% of the GD within 30 seconds and 99+% was neutralized within one hour.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A [chemical warfare agent] decontamination composition *for neutralizing chemical warfare agents or organophosphorus agricultural chemicals* comprising between 15% to 25%, by weight of a quaternary ammonium complex, about 15% to about 25% by weight of a selected oxidizer, and a non-toxic, non-flammable solvent, wherein said composition has a pH between 8 and 12.

2. The composition according claim 1, wherein the oxidizer is selected from the group consisting of the acids or salts of peracetate, perborate monohydrate, perborate tetrahydrate, monoperoxyphthalate, peroxymonosulfate, peroxydisulfate and percarbonate.

3. The composition according to claim 1, wherein the oxidizer is hydrogen peroxide.

4. The composition according to claim 1, wherein the quaternary ammonium complex consists of a mixture of benzyltrimethylammonium chloride and benzyltriethylammonium chloride.

5. The composition according to claim 4, wherein the mixture consists of a ratio of about 5 parts benzyltrimethylammonium chloride, by weight, to about 1 part benzyltriethylammonium chloride, by weight.

6. The composition according to claim 5, wherein the benzyltrimethylammonium chloride is about 16%, by weight, of the composition and the benzyltriethylammonium chloride is about 4%, by weight of the composition.

7. The composition according to claim 1, wherein the solvent is water.

8. The composition according to claim 7, wherein the solvent is about 25 to about 35%, by weight, of the composition.

9. The composition according to claim 1, wherein the solvent is a diol.

10. The composition according to claim 9, wherein the diol is selected from the group consisting of propylene glycol, 1,2-butanediol, 1,2-pentanediol, and 1,2-hexanediol.

11. The composition according to claim 10 wherein the diol is about 30%, by weight, of the composition.

12. The composition according to claim 1 further comprising a corrosion inhibitor.

13. The composition according to claim 12 wherein the corrosion inhibitor is selected from the group consisting of an amino alcohol, an amine or a polyamine.

14. The composition according to claim 1 wherein said composition further comprises a buffer, a stabilizer, a reaction catalyst or a preservative.

15. A [chemical warfare agent] decontamination [solution] *composition for neutralizing chemical warfare agents or organophosphorus agricultural chemicals* comprising:

about 10 to about 20%, by weight, of benzyltrimethyl ammonium chloride;

about 3 to about 10%, by weight, benzyltriethylammonium chloride;

about 20%, by weight hydrogen peroxide;

about 30%, by weight, inhibitor; and about 30%, by weight, water.

16. A method for [decontaminating] *neutralizing* chemical warfare agents *or organophosphorus agricultural chemicals* comprising the step of applying to a contaminated surface a [chemical warfare agent] decontamination composition comprising between 15% to 25%, by weight of a quaternary ammonium complex, about 15% to about 25% by weight of a selected oxidizer, and a non-toxic, non-flammable solvent, wherein said composition has a pH between 8 and 12.

17. The method according to claim 16, wherein the quaternary ammonium complex consists of a mixture of benzyltrimethylammonium chloride and benzyltriethylammonium chloride.

18. The method according to claim 17, wherein the oxidizer is selected from the group consisting of the acids or salts of peracetate, perborate monohydrate, perborate tetrahydrate, monoperoxyphthalate, peroxymonosulfate, peroxydisulfate and percarbonate.

19. The method according to claim 17, wherein the oxidizer is hydrogen peroxide.

20. A method for [decontaminating] *neutralizing* chemical warfare agents comprising applying to a [contaminated] surface *contaminated with* a chemical warfare agent *the* decontamination composition according to claim 15.

*21. A method for neutralizing organophosphorus agricultural chemicals comprising applying to a surface contaminated with an organophosphorus agricultural chemical the decontamination composition according to claim 15.*

* * * * *